US009200992B2

(12) United States Patent
Danylewych-May

(10) Patent No.: US 9,200,992 B2
(45) Date of Patent: Dec. 1, 2015

(54) SAMPLING SWAB

(75) Inventor: Ludmila L. Danylewych-May, North York (CA)

(73) Assignee: SMITHS DETECTION, Mississauga (CA)

( * ) Notice: Subject to any disclaimer, the term of this patent is extended or adjusted under 35 U.S.C. 154(b) by 0 days.

(21) Appl. No.: 13/562,118

(22) Filed: Jul. 30, 2012

(65) Prior Publication Data
US 2015/0185125 A1 Jul. 2, 2015

Related U.S. Application Data

(63) Continuation of application No. 11/326,599, filed on Jan. 6, 2006, now abandoned.

(60) Provisional application No. 60/642,091, filed on Jan. 10, 2005.

(51) Int. Cl.
| | |
|---|---|
| *G01N 1/02* | (2006.01) |
| *G01N 1/40* | (2006.01) |
| *A61B 10/00* | (2006.01) |
| *G01N 27/62* | (2006.01) |

(52) U.S. Cl.
CPC ............ *G01N 1/405* (2013.01); *A61B 10/0045* (2013.01); *G01N 1/02* (2013.01); *A61B 10/0051* (2013.01); *G01N 27/622* (2013.01); *G01N 2001/022* (2013.01); *G01N 2001/028* (2013.01)

(58) Field of Classification Search
CPC ................. G01N 2001/022; G01N 2001/028; A61F 13/38; A61F 13/385; A61B 10/0045; A61B 10/0051; A61B 10/0064; A61B 2010/0216

USPC .................................................. 600/569, 572
See application file for complete search history.

(56) References Cited

U.S. PATENT DOCUMENTS

| | | | | |
|---|---|---|---|---|
| 4,421,809 A | * | 12/1983 | Bish et al. ........................ | 428/90 |
| 4,748,065 A | | 5/1988 | Tanikella | |
| 5,037,611 A | | 8/1991 | Ledford, Jr. | |
| 5,162,652 A | | 11/1992 | Cohen et al. | |
| 5,457,316 A | | 10/1995 | Cohen et al. | |
| 5,491,337 A | * | 2/1996 | Jenkins et al. ................ | 250/287 |
| 5,571,976 A | | 11/1996 | Drolet | |
| 5,741,984 A | | 4/1998 | Danylewych-May et al. | |
| 5,854,431 A | * | 12/1998 | Linker et al. ................ | 73/863.23 |
| 5,859,362 A | | 1/1999 | Neudorfl et al. | |

(Continued)

FOREIGN PATENT DOCUMENTS

| | | |
|---|---|---|
| EP | 0 992 782 A1 | 4/2000 |
| WO | WO-03/029541 A1 | 4/2003 |

OTHER PUBLICATIONS

"Dupont Nomex Spunlaced Fabrics Type E88C: Technical Data Sheet." E.I. du Pont de Nemours and Company. 2003.*

(Continued)

*Primary Examiner* — Adam J Eiseman
(74) *Attorney, Agent, or Firm* — Foley & Lardner LLP

(57) ABSTRACT

A sampling swab useful in trace analyte detection is provided. The sampling swab possesses absorption/adsorption and desorption properties suitable for use trace analyte sample collection. The sampling swab is also capable of withstanding repeated high heat treatment and mechanical stress. A method for producing a sampling swab that is substantially free of impurities and detection interferants is also provided.

17 Claims, 5 Drawing Sheets

(56) References Cited

U.S. PATENT DOCUMENTS

| | | | |
|---|---|---|---|
| 5,859,375 | A | 1/1999 | Danylewych-May et al. |
| 5,928,176 | A | 7/1999 | Nakatani |
| 5,988,002 | A | 11/1999 | Danylewych-May et al. |
| 6,073,498 | A | 6/2000 | Taylor et al. |
| 6,073,499 | A | 6/2000 | Settles |
| 6,442,997 | B1 | 9/2002 | Megerle et al. |
| 6,627,444 | B1 | 9/2003 | Goledzinowski et al. |
| 6,642,513 | B1 * | 11/2003 | Jenkins et al. ............ 250/288 |
| 7,377,188 | B2 * | 5/2008 | Jenkins ................... 73/863.23 |
| 2006/0142668 | A1 * | 6/2006 | Triva ........................... 600/572 |

OTHER PUBLICATIONS

"Dupont Nomex Spunlaced Fabrics Type E88C: Technical Data Sheet", E.I. du Pont de Nemours and Company, 2003.

Advisory Action for U.S. Appl. No. 10/978,680, mail date Jun. 24, 2010, 3 pages.

Final Office Action U.S. Appl. No. 11/326,599 dated Jun. 25, 2009.

Non-Final Office Action U.S. Appl. No. 11/326,599 dated Feb. 18, 2009.

Non-Final Office Action U.S. Appl. No. 11/326,599 dated May 14, 2008.

Tan, Y. and DeBono, R. "IMS for Drugmaking". Today's Chemist At Work, Nov. 2004, pp. 15-16.

Hannum et al., "Miniaturized Explosives Preconcentrators for Use in Man-Portable Explosives Detection Systems", Security Technology, 2000, Proceedings IEEE 34th Annual 2000 International Carnahan Conference, pp. 222-227.

Supplementary European Search Report dated Jun. 16, 2010 issued in Application No. 06 84 7287.

* cited by examiner

Instrument Results (GC Narc - Non GC)     \*\*\*ALARM\*\*\*

Sample: 2.5ul of 4ng/ul buspiron in IsoPropyl     File: BUSPIRON-10NG-03.DRC
Context:

Time: 14:47:42    Date: 06/29/2004    Instrument: 400B - 12220    Des. Time: 30.00 s    Segs: 20
Temps: (°C): Drift Tube: 238   Inlet: 284   Desorber: 285     Flows (cc/min): Drift: 300   Sample: 0
Path: I:\New Tech\nomex + steel\BUSPIRON-10NG-03.DRC

SAMPLING SWAB

CROSS-REFERENCE TO RELATED APPLICATIONS

This application is a Continuation Application of U.S. Ser. No. 11/326,599 filed Jan. 6, 2006 which claims priority from U.S. Provisional Application Ser. No. 60/642,091 filed Jan. 10, 2005. The subject matter of each of the above-referenced applications is incorporated in entirety by reference.

BACKGROUND

Trace analyte detection is the detection of small amounts of analytes, often at nanogram to picogram levels. Trace analyte detection has numerous applications, such as screening individuals and baggage at transportation centers, mail screening, facility security applications, military applications, forensics applications, narcotics detection and identification, cleaning validation, quality control, and raw material identification. Trace analyte detection can be particularly useful for security applications such as screening individuals or items for components in explosive materials, narcotics or biological contaminants where small amounts of these components are deposited on the individual or on the outside of a package or bag.

Trace analysis is also important in pharmaceutical manufacturing. See, e.g. Tan and DeBono, *Today's Chemist at Work*, November 2004, pp. 15-16 and Munden et al., *Pharm. Tech. Eur.* Oct. 1, 2002. During the development of a manufacturing process and periodically thereafter, each piece of equipment must be verified, preventing contamination of pharmaceutical ingredient by contact with unclean equipment surfaces. Equipment surfaces are sampled and analyzed for trace contaminants. According to the Food and Drug Administration guidelines chemical residues in manufacturing equipment must be reduced to an acceptable level.

A variety of different techniques can be used for trace analyte detection. These methods include ion mobility spectrometry (IMS), mass spectrometry, gas chromatography, liquid chromatography, and high performance liquid chromatography (HPLC).

IMS is a particularly useful technique for rapid and accurate detection and identification of trace analytes such as narcotics, explosives, and chemical warfare agents. The fundamental design and operation of an ion mobility spetectometer is addressed in, for example, Ion Mobility Spectrometry (G. Eiceman and Z. Karpas, CRC Press, Boca Raton, Fla., 1994). IMS detects and identifies known analytes by detecting a signal which is unique for each analyte. IMS measures the drift time of ions through a fluid, such as clean, dry ambient air at atmospheric pressure. Analysis of analytes in a sample begins with collection of a sample and introduction of the sample into the spectrometer. A sample is heated to transform analyte from solid, liquid or vapor preconcentrated on a particle into a gaseous state. Analyte molecules are ionized in the reaction region of the IMS detector. Ions are then spatially separated in the IMS drift region in accordance to their ion mobility, which is an intrinsic property of an ion. In an IMS detector, where ions carrying a single charge are typically formed, ion mobility is roughly directly proportional to ion mass. An induced current at the collector generates a signature for each ion as a function of the time required for that ion to reach the collector. This signature is used to identify a specific analyte.

A variety of different methods can be used to introduce a sample into a detection instrument and the method will depend, in part, on the type of sample being analyzed and the detection technique. For example, U.S. Pat. Nos. 6,442,997, 6,073,499, 5,859,362, and 5,162,652 disclose devices for collecting vapor or air samples, U.S. Pat. No. 6,073,498 discloses a device for collecting fluid samples, U.S. Pat. No. 5,037,611 is directed to a method adsorbing gaseous samples on a tape, and U.S. Pat. No. 5,741,984 discloses a method which introduces a sample from a finger by pressing the finger on a sampling "token." U.S. Pat. Nos. 5,859,375 and 5,988,002 are directed to a methods and apparatus for collecting samples using a hand-held sampling device.

Another sampling method involves contacting an object or other substrate to be tested with a fabric sampling swab which collects analyte particles. Upon contact of a sampling swab with a substrate to be tested, solid sample particles can become imbedded into the porous structure of the textile swab. If the sample is in liquid form, the liquid can absorb into the fibers of the swab. In IMS, the swab is placed into the detection instrument and the sample thermally desorbed from the swab. A swab for use in IMS should have absorption and desorption properties suitable for the analytes and substrates to be sampled, should be compatible with the geometry and processes performed by the instrument, should be durable and stable over a range of temperatures, including temperatures in excess of 400° C., and should be substantially free from contaminants and impurities capable in interfering with sample analysis.

A sampling swab should have the ability to absorb and/or adsorb an analyte upon contact with the swab, as well as efficiently desorb the analyte from the swab upon placement of the swab in a detection instrument. For example, a sampling swab should be able to effectively absorb/adsorb volatile substances into its structure or embed sample particles into its porous structure upon contact with an analyte present on the test surface. Additionally, a sampling swab should not interfere with a desorption process of a sample analyte from its surface or fibers during desorption of the collected sample.

A suitable swab also should be durable and stable, capable of resisting chemical and physical decomposition and degradation due to heating and mechanical stress. Decomposition and degradation of a swab can lead to contamination of the detection instrument, thus compromising the integrity of the analysis and potentially fouling the detection instrument. Decomposed and degraded fibers can generate false positives or can interfere with analyte detection resulting in failure in detecting an analyte. In addition, decomposed and degraded fibers can remain in the detection instrument, thus compromising subsequent analyses and risking damage to the detection instrument. The resistance of a swab to decomposition and degradation is affected by physical properties of materials used.

The stability of a textile fiber at high temperatures is particularly important in detection methods involving heating the swab. For example, in ion mobility spectrometry, the swab is heated to desorb and vaporize analyte molecules collected by contact of the swab with a substrate being tested. Thus, it is desirable for the swab to resist decomposition and degradation at temperatures in excess of 400° C. for durations of at least one minute.

It is also desirable that a swab is substantially free of impurities which may interfere with the detection of analytes. These impurities can interfere with the analyte detection by creating unacceptable background signal which swamps out analyte signal and can also cause instrument contamination and instrument failure.

Thus, there is a need for a textile processing and cleaning protocol which results in a swab which is clean and while maintaining sufficient strength and structural integrity.

SUMMARY OF THE INVENTION

Thus, there is need in the art for a sampling swab and a method of manufacturing a sampling swab, having absorption and analyte collection efficiency together with desorption properties suitable for trace analyte sample collection, which is capable of withstanding repeated mechanical stress and heat treatment.

One embodiment provides a sampling swab comprising a synthetic fiber, wherein the swab is heated to reduce detection interferants.

Another embodiment provides a method of processing a synthetic fabric comprising heating the fabric at an oven temperature of between 120° C. to 400° C. for a time of between 1 to 60 minutes.

A further embodiment provides a sampling swab produced by steps comprising heating the cotton fabric to a temperature between approximately 200° C. to approximately 250° C. for a time of between approximately 5 to approximately 15 minutes.

These and other features, aspects, and advantages of the present invention will become apparent from the following description, appended claims, and the accompanying exemplary embodiments shown in the drawings, which are briefly described below.

It is to be understood that both the foregoing general description and the following detailed description are exemplary and explanatory only, and are not restrictive of the invention as claimed.

DETAILED DESCRIPTION

Figure 1A:
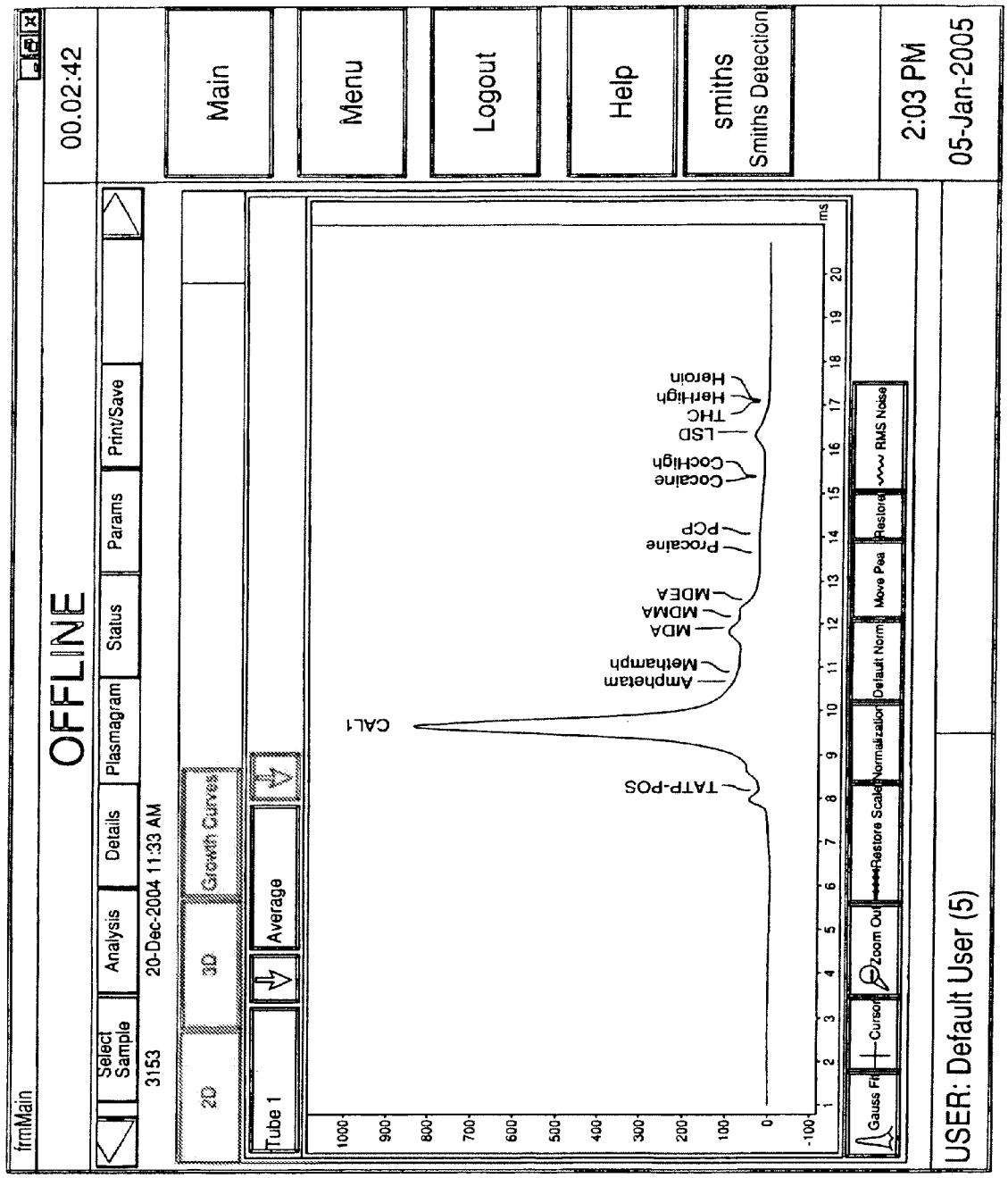
FIG. 1. Plasmagram of clean sampling swab obtained using Ionscan® 500 DT ion mobility spectrometer (Smiths Detection). (A) Negative mode parameters: negative ionization mode, drift tube temperature of 111° C., inlet temperature of 240° C., desorber temperature of 225° C. The ionization reagent is hexachloroethane, the drift gas is cleaned, dried room air at a flow rate of 350 cm$^3$/min. The scan period is 22 ms with a 0.200 ms shutter gate pulse, 0.025 s analysis delay, 6.600 s analysis duration, 20 co-added scans per segment, and 15 segments per analysis. (B) Positive mode parameters: positive ionization mode, drift tube temperature of 237° C., inlet temperature of 280° C., desorber temperature of 285° C. The ionization reagent is nicotinamide and drift gas is cleaned, dried room air at a flow rate of 350 cm$^3$/min. The scan period is 20 ms with a 0.200 ms shutter gate pulse, 0.025 s analysis delay, 8.000 s analysis duration, 20 co-added scans per segment, and 20 segments per analysis.

The invention provides a sampling swab with advantageous properties for sample collection in trace analyte detection. Qualities that impart the ability of a swab to function effectively include, but are not limited to sample collection efficiency, durability, and purity.

Unless indicated otherwise, all technical and scientific terms are used in a manner that conforms to common technical usage. Generally, the nomenclature of this description and the described procedures and techniques are well known and commonly employed in the art. "Approximately," as it is used herein, generally refers to a variation of 10% to 20% from a given value and is meant to allow for error inherent in measurement techniques as well as differences in measurement values that can be obtained when measurements are performed using different techniques.

A. Sampling Swab Uses and Performance Properties

A sampling swab can be used for sample collection in any suitable trace detection technique. Suitable detection techniques include, but are not limited to IMS, mass spectrometry, and gas chromatography, liquid chromatography, and high performance liquid chromatography and combinations of these methods. In one embodiment, a swab is used to collect samples for IMS.

Sampling swabs are useful for collecting samples containing of a wide range of analytes, including but not limited to explosives, narcotics, chemical warfare agents, toxins, pharmaceutical process contaminants, and other chemical compounds. "Sample" refers, without limitation, to any molecule, compound or complex that is adsorbed, absorbed, or imbedded on or within a sampling swab. A sample can contain an analyte of interest, referred to herein as an "analyte" or "sample analyte," which is understood to be any analyte to be detected using a detection technique.

Explosives which can be collected using a swab include, but are not limited to, 2-amino-4,6-dinitrotoluene, 4-amino-2,6-dinitrotoluene, ammonal, ammonium nitrate, black powder, 2,4-dimethyl-1,3-dinitrobutane, 2,4-dinitrotoluene, ethylene glycol dinitrate, forcite 40, GOMA-2, hexanitrostilbene, 1,3,5,7-tetranitro-1,3,5,7-tetrazacyclooctane (HMX), mononitrotoluene, nitroglycerine, pentaerythritol tetranitrate (PETN), 1,3,5-trinitro-1,3,5-triazacyclohexane (RDX), semtex-A, Semtex-H, smokeless powder, trinitro-2,4,6-phenylmethylnitramine tetryl (Tetryl), 2,4,6-trinitrotoluene (TNT), trilita, and 1,3,5-trinitrobenzene and combinations of these compounds. In one embodiment, the explosive which are collected are 1,3,5-trinitro-1,3,5-triazacyclohexane, pentaerythritol tetranitrate, 2,4,6-trinitrotoluene, trinitro-2,4,6-phenylmethylnitramine tetryl, nitroglycerine, ammonium nitrate, 3,5,7-tetranitro-1,3,5,7-tetrazacyclooctane, and combinations thereof. Narcotics which can be collected using a swab include, but are not limited to 6-acetylmorphine, alprazolam, amobarbital, amphetamine, antipyrine, benzocaine, benzoylecgonine, bromazepam, butalbital, carbetapentane, cathinone, chloradiazepoxide, chlorpheniramine, cocaethylene, cocaine, codeine, diazepam, ecgonine, ecognine methyl ester (EME), ephedrine, fentanyl, flunitrazepam, hashish, heroin, hydrocodone, hydromorphone, ketamine, lidocaine, lorazepam, lysergic acid diethylamide (LSD), lysergic acid, N-methyl-1-3(3,4-methylenedioxyohenyl)-2-butanamine (MBDB), 3,4-methylenedioxyamphetamine (MDA), DL-3,4-methyl enedioxyethylamphetamine (MDEA), methylenedioxymethamphetamine (MDMA), marijuana, mescaline, methadone, methamphetamine, methaqualone, methcathinone, morphine, noscapine, opium, oxazepam, oxycodone, phencyclidine (PCP), pentobarbital, phenobarbital, procaine, psilocybin, secobarbital, temazepam, THC, THC—COOH, and triazolam. In one embodiment, the narcotics which can be collected with a swab include cocaine, heroin, phencyclidine, THC, methamphetamine, methylenedioxyethylamphetamine, methylenedioxymethamphetamine, N-methyl-1-3(3,4-methylenedioxyohenyl)-2-butanamine, lysergic acid diethylamide, and combinations thereof.

Chemical warfare agents and other toxins that can be collected using a swab include, but are not limited to amiton (VG), anthrax, arsine, cyanogen chloride, hydrogen chloride, chlorine, diphosgene, PFIB, phosgene, phosgene oxime, chloropicrin, ethyl N,N-dimethyl phosphoramicocyanidate (Tabun), isopropyl methyl phosphonofluoridate (Sarin), pinacolyl methyl phosphonefluoridate (Soman), phosphonofluoridic acid, ethyl-, isopropyl ester (GE), phosphonothioic acid, ethyl-, S-(2-(diethylamino)ethyl)O-ethyl ester (VE), phosphonothioic acid, methyl-, S-(2-(diethylamino)ethyl)O-ethyl ester (VM), distilled mustard, ethyldichloroarsine, lewisite 1, lewisite 2, lewisite 3, methyldichloroarsine, mustard-lewisite mixture, mustard-T mixture, nitrogen mustard 1, nitrogen mustard 2, nitrogen mustard 3, phenyldichloroarsine, phosgene oxime, sesqui mustard, adamsite, aflatoxin, botulinus toxin, ricin, saxitoxin, trichothecene mycotoxin, methylphosphonothioic acid S-(2-(bis(1-methylethyl) amino)ethyl)O-ethyl ester (VX), cyclohexyl methylphosphonofluoridate (GF), and combinations thereof.

Pharmaceutical process contaminants refers to any compound present on pharmaceutical manufacturing equipment, such as resulting from cross-contamination, which can adulterate an active pharmaceutical ingredient, excipient, or other pharmaceutical production materials. For example, a first compound is produced in a vat using a mixture of chemical ingredients and it is desired to use the same vat for a subsequent production run of a second compound. It is important that the first compound and materials from the production run not contaminate the second production run and thus cleaning is necessary. Such contaminants include, but are not limited to include detergents, sugars and other active pharmaceutical ingredients such as acetaminophen, alprazolam, baclofen, chlorpheniramine malate, chlorpromazine, ibuprofen, morphine, naproxen, oxycodone, pseudoephedrine, sennoside, and triclosan.

Sample analytes can be collected onto a swab by any suitable means. For example, a sample containing analytes of interest can be collected onto a swab by direct contact of the swab with the substrate to be tested, e.g., by mechanical agitation or frictional contact. Direct contact can be achieved by direct manual contact of an article with the swab or insertion of swab material into a holder which manually or automatically directly contacts an article with the swab material. Manual rubbing can be accomplished using devices and methods described in, e.g., U.S. Pat. Nos. 5,859,375 and 5,988,002. Sample analytes can also be collected onto a swab by drawing a gaseous environment over or through the swab such that analytes become associated with the swab. Additionally, sample analytes can be collected by mounting swab material into a vacuum device. In one embodiment, the vacuum device is a hand-held device. In another embodiment, sample analytes can be collected onto a swab using a combination of vacuum with frictional contact, i.e., by rubbing or brushing an article to be tested while drawing a vacuum over the swab. A substrate to be tested can include any person or object. For example, a substrate can be a personal effect, clothing, bag, luggage, furniture, automobile interior, pharmaceutical process equipment, etc. Alternatively, environment to be sampled can be pumped through a swab to collect a sample.

Adsorption and absorption of analytes onto a swab should be at least partially reversible. Accordingly, an analyte should be capable of being at least partially desorbed from a swab on which the analyte is adsorbed and/or absorbed. An analyte can be desorbed from a swab by any means appropriate for a given detection technique. By this, it is meant that a swab can be treated in any way necessary to prepare a sample for analysis. This treatment can depend, in part, on the type of analytes present in a sample and on the detection technique. Analytes can be desorbed from a swab though mechanical or thermal means. In one embodiment, an analyte can be desorbed from a swab by means of thermal desorption, wherein a swab is heated to vaporize the analyte. Analytes can also be desorbed from a swab by extraction of an analyte from a swab into a solvent. Without limitation, any suitable solvent can be used. Analyte-containing solvent can then be transferred to a detection instrument by any suitable means such as, for example, a syringe.

In one embodiment, analytes in a sample for analysis by ion mobility spectrometry are desorbed from a swab using thermal desorption.

B. Sampling Swab Composition

A swab suitable for use in trace analyte collection and detection should be durable and capable of resisting decomposition or degradation due to heating and mechanical stress. The resistance of a swab to decomposition and degradation when subjected to repeated mechanical and temperature stress is affected by physical properties of materials used, such as fiber composition, fiber strength, fiber length and fiber diameter.

As used herein, "swab" and "sampling swab" are used interchangeably. "Swab" and "sampling swab" refers to a woven or non-woven fabric of any suitable material. In one embodiment, the fabric is comprised a synthetic fiber such as of Kevlar®, Nomex® or a combination of Kevlar® and Nomex®. Kevlar and Nomex are trademarks of the E. I. DuPont Co. for its brands of aromatic polyamide (aramid) fibers. The fibers can be homogeneous or heterogeneous. By homogeneous it is meant that a fiber is of uniform composition. By heterogeneous it is meant that a fiber contains both more than one component which can optionally be arranged as longitudinal layers within an individual fiber. For example, a fiber can comprise both Nomex and Kevlar within a single fiber or a fabric can comprise homogeneous fibers of both Nomex and Kevlar. In one embodiment the Nomex material is any of Nomex® R E88C, (specified as 320B), Nomex® MC 59207 (specified as 326A), Nomex® R E88C spunlaced fabric (specified as 320A), Nomex® MC 59032, Nomex® R E88C spunlaced fabric, or a combination of these materials. In another embodiment, the Nomex material is any of Nomex® R E88C, (specified as 320B), Nomex® MC 59207 (specified as 326A), Nomex® R E88C spunlaced fabric (specified as 320A), or a combination of these materials.

The shape of the swab can be, without limitation, circular, oval, square, rectangular, or any other shape suitable to purpose of the swab.

C. Factors Contributing to Sampling Swab Performance

The ability of a swab to absorb and/or adsorb analytes upon contact with a substrate to be tested and efficiently desorb analytes when placed in a detection instrument is affected, in part, by the air permeability, density and thickness of a swab.

A swab should have suitable air permeability. The air permeability of a substance is a measure of its ability of air to pass through the fabric at a predetermined rate. Suitable air permeability is useful in detection techniques where a gas is pushed through the swab to sweep analytes from the swab into the detection instrument. For example, in IMS, the swab is place into the instrument, a desorber heater vaporizes the sample, which is swept by a gas flow into an ionization region where the analytes are ionized. If a swab does not have sufficient air permeability, an IMS instrument can experience a pressure fault causing instrument failure.

In the scenario in which a sample is being collected with a high volume sampler a suitable maximum swab air permeability is the range of approximately 80 cubic feet/minute (CFM) to approximately 125 CFM.

Air permeability can be measured by any suitable means. For example, air permeability can be measured using the standard methods provided in ASTM D737 and CAN/CGSB 4.2 No. 36.

Porosity is a function of the size and frequency of pores in a fabric. Pores, minute channels or open spaces in a solid substance, aid in adsorption or absorption of an analyte onto a swab and retention of analytes upon contact. densometer. Densometers measure the time required for a given volume of air to flow through a standard area of material being tested. Densometers are an accepted standard for measuring the porosity, air-permeability and air-resistance of sheet-like and woven materials.

The density and thickness of a swab also can affect both the collection and desorption efficiency as well as the swabs durability. A swab which is too dense or too thick can have an unacceptably high heat capacity, which can result in a poor desorption efficiency. Suitable swab density ranges from approximately can have a weight per unit area of between approximately $0.010$ $g/cm^2$ to approximately $0.8$ $g/cm^2$. In one embodiment a swab has a density of between approximately $0.4$ $g/cm^2$ to approximately $0.71$ $g/cm^2$. In another embodiment, a swab has a density of between approximately $0.6$ $g/cm^2$ to approximately $0.71$ $g/cm^2$. A swab can also have a thickness of between approximately 0.01 cm to approximately 0.03 cm. In one embodiment, a swab as a thickness of between approximately 0.05 mm to approximately 0.15 mm. In one embodiment, a swab has a thickness of between approximately 0.10 mm and 0.15 mm. Density and thickness and density can be determined by any means known in the art such as, for example, measurement using a densometer.

The stability of swab fiber at high temperatures is particularly important in detection methods which involve heating the swab. For example, in ion mobility spectrometry, a sampling swab is heated to desorb and vaporize sample particles collected by contact of the swab with a tested material. Thus a swab should be resistant to decomposition or degradation at high temperatures.

Although it is desirable for a swab to be stable at certain temperatures indefinitely, the stability a swab at temperatures disclosed by the present invention refers to the stability of the swab at the specific temperature for at least 10 seconds, 1 minute, at least 2, minutes, at least 4 minutes, at least 6 minutes, at least 8 minutes, at least 10 minutes, at least 15 minutes, at least 20 minutes, at least 25 minutes, at least 30 minutes, or at least 1 hour. This time refers to the time over the duration of a single exposure or over the duration of the usable lifetime of the swab.

In one embodiment, a swab resists degradation up to a temperature of at least 300° C., at least 325° C., at least 350° C., at least 400° C., at least 450° C., or at least 500° C. In another embodiment, a swab resists degradation up to a temperature of approximately 300° C. for approximately 1 minute to approximately 5 minutes. In a further embodiment, a swab resists degradation up to a temperature of approximately 300° C. for approximately 2 minutes.

D. Method of Producing Sampling Swabs

The inventors also discovered a method treating a synthetic fabric or fiber to reduce detection interferants yielding a swab useful for collecting samples for trace analyte detection. The method produces a swab essentially free of impurities that can interfere with trace analyte detection, but which is capable of withstanding repeated mechanical and thermal stress without degradation or loss of structural integrity.

"Detection interferants" refers to any impurity or contaminant present on the fabric or fiber of a swab which can prevent (or mask) detection of an analyte or cause a detection instrument to produce a false positive identification. A detection interferant is considered "reduced" if the amount of interferant is decreased such that masking of an analyte or production of a false positive does not occur.

A method for removing impurities which interfere with trace detection analysis comprises heating the swab material at a temperature of between 120° C. and 400° C. for one to thirty minutes. In one embodiment, swab material is heated at a temperature of approximately 200° C. to approximately 350° C. In a further embodiment, the swab material is hearted at approximately 250° C.

Heating can be performed using any means known in the art. In one embodiment, heating is performed in a forced air oven. Heating can be performed for from approximately 1 minute to approximately 60 minutes. In one embodiment, heating is performed for at least 1 minute, at least 2, minutes, at least 4 minutes, at least 6 minutes, at least 8 minutes, at least 10 minutes, at least 15 minutes, at least 20 minutes, at least 25 minutes, at least 30 minutes, or at least 60 minutes.

E. Quality Control Testing of Sampling Swabs

After processing and manufacturing of a sampling swab, either before or after the swabs are cut to size or packaged, a swab can be tested for impurities or contaminants which can interfere with the detection of the desired analyte(s) on the processed swab. Other desirable performance characteristics, such as, for example, suitable adsorption/absorption and desorption properties and general compatibility with a detection instrument, can be tested as well.

A swab can be tested for purity by analyzing a clean swab using any suitable detection method. A swab can be tested for desirable performance characteristics by placing a known analyte sample onto the swab and analyzing the known swab using a suitable detection method. Results obtained from a known analyte sample can be compared to acceptable minimum standards for certification of acceptable quality.

Swabs can be tested using any appropriate method. For example, it can be desirable to test a swab using the detection method for which the swab is intended. In one embodiment, a swab is tested using ion mobility spectrometry.

The following examples are given to illustrate the present invention. It should be understood, however, that the present invention is not to be limited to the specific embodiments described in these examples. It will be apparent to those skilled in the art that various modifications and variations can be made to the embodiments of the present invention without departing from the spirit or scope of the present invention. Thus, it is intended that the present invention covers other modifications and variations of this invention within the scope of the appended claims and their equivalents.

Example 1

Sensitivity Testing and Optimization of Baking Conditions

This example describes optimization of swab material selection and preparation for Nomex® swabs. Several types of Nomex® material are tested with respect to their background interferences, sensitivities, particle pick-up efficiency from the surface, particle retention on the swab and durability after extensive swabbing and analysis. This study is performed using a Sabre 2000 IMS trace detection device (Smiths Detection) in all operational modes (negative, positive, CW negative, CW positive).

All tests are performed using Sabre 2000 SN 20478 operating at standard settings of control parameters for each mode. Table 1 provides pertinent parameters for each mode. The sensitivity of the machine is checked every morning using standard TNT or cocaine solutions. Oxygen detection is used and purification cartridges are replaced as necessary.

TABLE 1

Control parameters used in the course of this study.

| | Mode of operation | | | |
|---|---|---|---|---|
| Parameter | Reg. Neg. | Reg. Pos. | CW Neg. | CW Pos. |
| T (drift), ° C. | 110 | 130 | 105 | 105 |
| T (inlet), ° C. | 180 | 190 | 145 | 145 |
| T (des), ° C. | 190 | 190 | 145 | 145 |
| T (cal), ° C. | 58 | 60 | 60 | 65 |
| V (drift), cc/min | 200 | 200 | 200 | 200 |
| V (sample), cc/min | 110 | 110 | 110 | 110 |

The following Nomex® materials were tested:
1. Nomex® R E88C, d=2.0 oz/sq. yd. (style 320B)
2. Nomex® MC 59207, d=2.6 oz/sq. yd. (style 326A)
3. Nomex® R E88C, brand spunlaced fabric, d=2.0 oz/sq. yd (style 320A)
4. Nomex® MC 59032, d=2.0 oz/sq. yd.
5. Nomex® R E88C, brand spunlaced fabric, d=0.9 oz/sq. yd.

The material #5 is excluded from further testing, because it was too thin for the application. The material #4 is also excluded because excessive static formation made it unsuitable for the application.

Figure 1B:
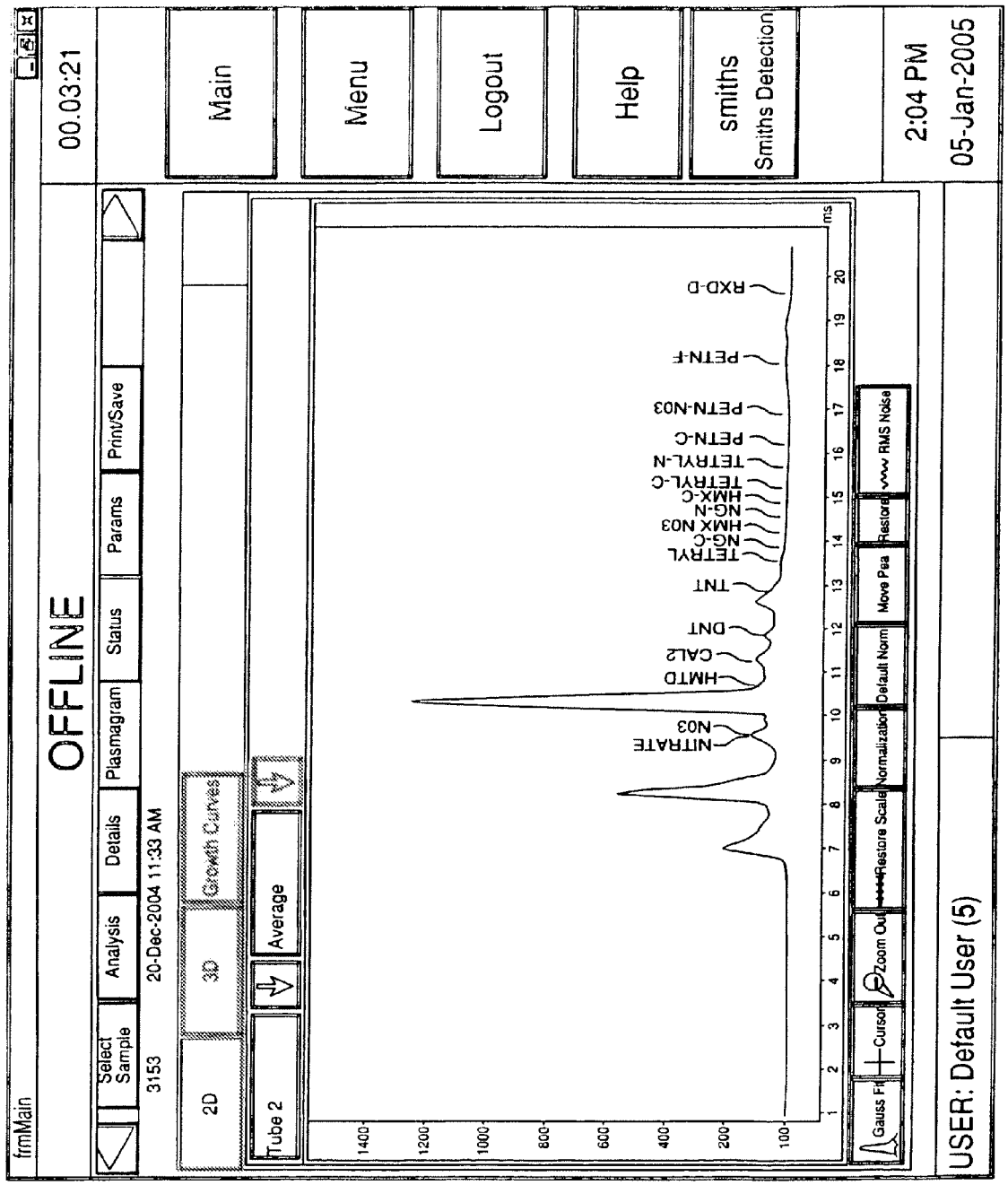

1. Sensitivity Test in the Negative Mode
   a. IMS Background of Nomex® Materials Three Nomex® materials were tested: 320B, 326A and 320A. All three show similar background plasmagrams. An exemplary plasmagram is provided in FIG. 1. A peak near the TNT peak with $K_0$=1.4970 (A=200-300 du) and contamination peak ($K_0$=1.8280) with similar intensity are typically present. Occasionally, a small peak interferes with nitrate (less than 100 du) and a small TATP-S interference peak (about 100 du) is observed. After four consecutive desorptions, the interference peak close to TNT is reduced to less than 100 du, although the contamination peak ($K_0$=1.8280) remains unchanged. Nitrate and TATP interferences are removed.

b. Sensitivity of Explosives on Nomex® Swab Materials

Standard solutions of explosives with concentrations at the detection level or close to it are used. The instrument response to 4 ng of TNT and PETN is tested using:
1. unbaked Nomex® swabs,
2. the swabs after several consecutive desorptions and
3. swabs baked for 10 min at 200° C.

Figure 2:
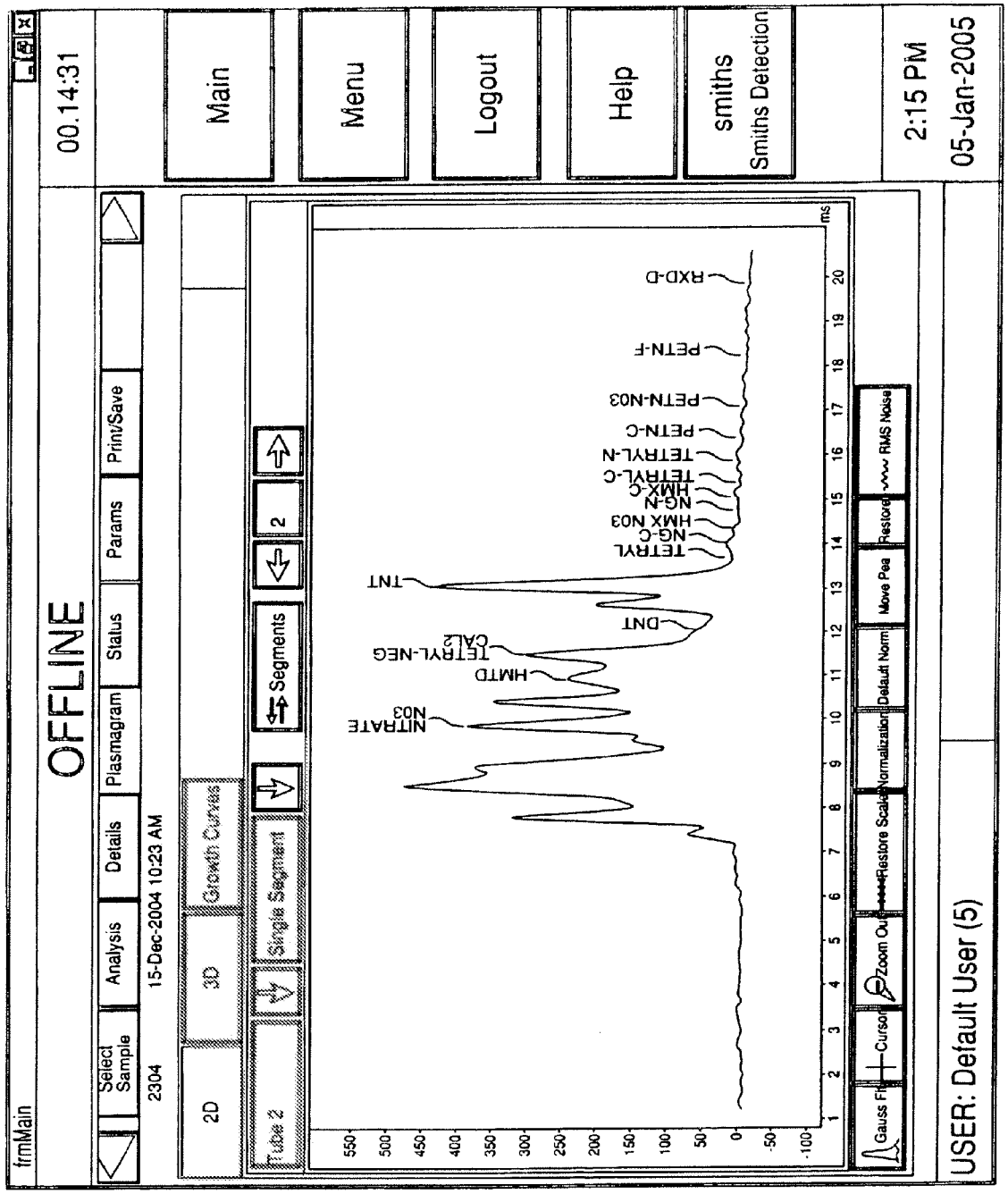
FIG. 2. Plasmagram of 4 ng TNT on a sampling swab obtained using Ionscan® 500 DT ion mobility spectrometer (Smiths Detection) run with following parameters: negative ionization mode, drift tube temperature of 111° C., inlet temperature of 240° C., desorber temperature of 225° C. The ionization reagent is hexachloroethane, the drift gas is cleaned, dried room air at a flow rate of 350 cm3/min. The scan period is 22 ms with a 0.200 ms shutter gate pulse, 0.025 s analysis delay, 6.600 s analysis duration, 20 co-added scans per segment, and 15 segments per analysis.

An exemplary plasmagram is provided in FIG. 2 and the data is provided in Tables 2 and 3.

TABLE 2

Sensitivity of 4 ng TNT deposited on Nomex ® swabs after different swab treatments.

| Material | Treatment | Max A | Cum A | t (max) |
|---|---|---|---|---|
| 320A | unbaked, 1st desorption | No response | No response | |
| | unbaked, 5th desorption | 190 | 1109 | |
| | unbaked, 10th desorption | 291 | 2397 | |
| | baked 10 min @ 200° C. | 374 ± 38 | 3696 ± 538 | 3.5 s |
| 320B | unbaked, 1st desorption | 81 | 500 | |
| | unbaked, 5th desorption | 265 | 2711 | |
| | unbaked, 10th desorption | 320 | 3521 | |
| | baked 10 min @ 200° C. | 375 ± 23 | 3842 ± 379 | 3.5 s |
| 326A | unbaked, 1st desorption | 109 | 393 | |
| | unbaked, 5th desorption | 328 | 3009 | |
| | unbaked, 10th desorption | 419 | 4128 | |
| | baked 10 min @ 200° C. | 381 ± 60 | 3783 ± 822 | 3.8 s |
| Shark Skin | N/A | 347 ± 29 | 3894 ± 348 | 3.0 s |

Shark Skin swab data provided for comparison to cellulosic swab material. The last column specifies the desorption time at which the maximum intensity was observed.

TABLE 3

Sensitivity of 4 ng PETN deposited on Nomex ® swabs after different swab treatments.

| Material | Treatment | Max A | Cum A | t (max) |
|---|---|---|---|---|
| 320A | unbaked, 1st desorption | 150 | 758 | |
| | unbaked, 5th desorption | 219 | 1684 | |
| | unbaked, 10th desorption | 327 | 2919 | |
| | baked 10 min @ 200° C. | 315 ± 41 | 2914 ± 363 | 3.5 s |
| 320B | unbaked, 1st desorption | 139 | 955 | |
| | unbaked, 5th desorption | 263 | 2503 | |
| | unbaked, 10th desorption | 280 | 2504 | |
| | baked 10 min @ 200° C. | 331 ± 17 | 3248 ± 286 | 3.5 s |
| 326A | unbaked, 1st desorption | 162 | 994 | |
| | unbaked, 5th desorption | 305 | 3070 | |
| | unbaked, 10th desorption | 269 | 2518 | |
| | baked 10 min @ 200° C. | 281 ± 33 | 2509 ± 462 | 3.5 s |
| Shark Skin | N/A | 356 ± 27 | 4076 ± 415 | 3.5 s |

Shark Skin swab data provided for comparison to cellulosic swab material. The last column specifies the desorption time at which the maximum intensity was observed.

The sensitivity of TNT and PETN on unbaked Nomex® swabs is poor, particularly for TNT where, depending on the swab, either no response is observed or the maximum intensity is 25% of the baked Nomex® or Shark Skin swabs responses. The sensitivities of TNT and PETN on baked Nomex® swabs are very similar on all swabs and comparable with sensitivities obtained on Shark Skin swabs.

Sensitivities of various explosives on Nomex® swabs baked for 10 min at 200° C. is also examined. This data is provided in Table 4.

TABLE 4

Sensitivities of explosives on baked (10 min at 200° C.) Nomex ® swabs.

| Material | Max A | Cum A | t (max) |
|---|---|---|---|
| | RDX (4 ng) | | |
| 320A | 394 ± 32 | 5013 ± 586 | 4.5 s |
| 320B | 420 ± 54 | 5270 ± 707 | 4.5 s |
| 326A | 365 ± 52 | 4982 ± 480 | 5 s |
| Shark Skin | 412 ± 43 | 5264 ± 563 | 4 s |

TABLE 4-continued

Sensitivities of explosives on baked (10 min at 200° C.) Nomex ® swabs.

| Material | Max A | Cum A | t (max) |
|---|---|---|---|
| NG (4 ng) | | | |
| 320A | 190 ± 25 | 1567 ± 261 | 2.3 s |
| 320B | 197 ± 25 | 1579 ± 257 | 1.7 s |
| 326A | 190 ± 19 | 1603 ± 258 | 2.6 s |
| Shark Skin | 280 ± 59 | 2716 ± 772 | 2.7 s |
| AN (200 ng) | | | |
| 320A | 1047 ± 119 | 16714 ± 2931 | 3.2 s |
| 320B | 1001 ± 174 | 15742 ± 4501 | 3.5 s |
| 326A | 1036 ± 79 | 16519 ± 1976 | 4.0 s |
| Shark Skin | 779 ± 160 | 10417 ± 2883 | 4.0 s |
| DNT (100 ng) | | | |
| 320A | 143 ± 33 | 1819 ± 424 | 3.7 |
| 320B | 130 ± 14 | 1650 ± 424 | 3.5 |
| 326B | 152 ± 30 | 2029 ± 355 | 4 s |
| Shark Skin | 119 ± 17 | 1503 ± 188 | 3.5 s |
| TATP (2 ug) | | | |
| 320A | 449 ± 25 | 3154 ± 591 | 2.5 s |
| 320B | 498 ± 43 | 3361 ± 645 | 2.4 s |
| 326A | 484 ± 64 | 3993 ± 367 | 2.8 s |
| Shark Skin | 429 ± 32 | 2621 ± 563 | 2.5 s |

Shark Skin swab data provided for comparison to cellulosic swab material. The last column specifies the desorption time at which the maximum intensity was observed.

Sensitivities of various explosives on Nomex® 320B swabs baked for 15 min at 250° C.) is determined. The results are provided in Table 5.

TABLE 5

Sensitivities of explosives on Nomex ® 320B swabs baked for 15 min at 250° C.

| Substrate | Max A | Cum A | t (max) |
|---|---|---|---|
| TNT (4 ng) | | | |
| Nomex ® 320B | 284 ± 13 | 3133 ± 144 | 3.5 s |
| Shark Skin | 224 ± 25 | 2425 ± 250 | 3 s |
| PETN (4 ng) | | | |
| Nomex ® 320B | 178 ± 11 | 1743 ± 226 | 3.5 s |
| Shark Skin | 164 ± 13 | 1551 ± 183 | 3.5 s |
| RDX (4 ng) | | | |
| Nomex ® 320B | 196 ± 14 | 2436 ± 250 | 4.5 s |
| Shark Skin | 172 ± 38 | 2051 ± 524 | 4 s |
| NG (4 ng) | | | |
| Nomex ® 320B | 102 ± 19 | 788 ± 304 | 2.9 s |
| Shark Skin | 100 ± 30 | 575 ± 288 | 2.6 s |

Shark Skin swab data is specified for comparison. The last column specifies the time at which maximum intensity was observed.

2. Sensitivity Test in the Positive Mode a. IMS Background of Nomex® Materials

As in the negative mode, three Nomex® materials are tested: 320B, 326A and 320A. The background of these materials is tested after pre-baking for 10 min at 200° C. as in the negative mode.

All baked Nomex® materials show similar background plasmagrams with slightly different intensities of interfering peaks. Three ion peaks are observed:

1. $K_0$=1.3585, d=15.575 ms, A=100-150 du,
2. $K_0$=1.4955, d=14.150 ms, A=600-1000 du,
3. $K_0$=2.0270, d=10.440 ms, A=100-150 du.

No false alarms for any of the nine analytes are detected. No major changes in the intensity of background peaks are observed during several consecutive desorptions.

Nomex® swabs are then baked at higher temperatures for longer periods of time and the intensity of background peaks monitored. The sensitivity of cocaine is tested for each batch of baked swabs. Table 6 contains the intensity of background peaks at various baking conditions. The highest background peaks are observed for Nomex® 326A, the thickest of the materials. These peaks could be reduced only at higher baking temperatures. The "cleanest" background and quickest disappearance of the major background peak ($K_0$=1.4955) is observed for Nomex® 320B.

TABLE 6

Intensity of background peaks of Nomex ® materials at various baking conditions.

| | | Peak Intensity (du) | | |
|---|---|---|---|---|
| Material | Baking conditions | $K_0$ = 1.3585 d = 15.57 ms | $K_0$ = 1.4955 d = 14.15 ms | $K_0$ = 2.0270 d = 10.44 ms |
| 320A | 10 min @ 200° C. | 120 | 800 | 160 |
| | 15 min @ 250° C. | 200 | 450 | 200 |
| | 30 min @ 250° C. | 200 | 260 | 200 |
| | 30 min @ 270° C. | 180 | 170 | 170 |
| 320B | 10 min @ 200° C. | 130 | 600 | 150 |
| | 15 min @ 250° C. | 160 | 120 | 130 |
| | 30 min @ 250° C. | 160 | 75 | 100 |
| | 30 min @ 270° C. | 110 | 40 | 100 |
| 326A | 10 min @ 200° C. | 70 | 1000 | 100 |
| | 15 min @ 250° C. | 200 | 600 | 200 |
| | 30 min @ 250° C. | 200 | 450 | 200 |
| | 30 min @ 270° C. | 100 | 160 | 75 | b. Sensitivity of Narcotics Detection on Nomex® Materials

Standard solutions of narcotics at the detection level are used. The sensitivity of cocaine is tested using Nomex® swabs baked at different conditions. The upper section of Table 7 shows these results. The resulting sensitivities are compared with those obtained using standard Shark Skin swabs. Maximum sensitivity for cocaine is obtained when Nomex® swabs baked are baked for 15 minutes at a temperature of 250° C. No additional sensitivity is gained by baking the swabs for a longer time or at a higher temperature.

Sensitivity testing of Nomex® swabs the for methamphetamine and heroin is conducted with Nomex® swabs baked are baked for 15 minutes at a temperature of 250° C.

In general, the sensitivities of narcotics on Nomex® swabs are equal or lower compared with Shark Skin swabs depending on analyte and swab baking conditions. Considering only swabs baked for 15 min at 250° C., the percentage of signal intensity reduction on Nomex® swabs in relation to Shark Skin swabs was as follows:

Cocaine: swab 320A: 0%
    swab 320B: 0%
    swab 326A: 30% (within variability range)
Methamphetamine: swab 320A: 30%
    swab 320B: 20%
    swab 326A: 15%
Heroin: swab 320A: 50%
    swab 320B: 30%
    swab 326A: 65%

TABLE 7

Sensitivities of narcotics deposited as a solution on Nomex ® swabs.

| Material | Treatment | Max A | Cum A | t (max) |
|---|---|---|---|---|
| COCAINE (5 ng) | | | | |
| 320A | baked 10 min @ 200° C. | 130 ± 20 | 891 ± 157 | 4 s |
|  | baked 15 min @ 250° C. | 215 ± 37 | 1501 ± 302 | 4 s |
|  | baked 30 min @ 250° C. | 224 ± 17 | 1543 ± 120 | 4.5 s |
|  | baked 30 min @ 270° C. | 229 ± 19 | 1682 ± 193 | 5.5 s |
| 320B | baked 10 min @ 200° C. | 178 ± 21 | 1349 ± 194 | 4.5 s |
|  | baked 15 min @ 250° C. | 242 ± 15 | 1818 ± 150 | 5 s |
|  | baked 30 min @ 250° C. | 247 ± 21 | 1792 ± 142 | 4.5 s |
|  | baked 30 min @ 270° C. | 249 ± 9 | 1868 ± 179 | 5 s |
| 326A | baked 10 min @ 200° C. | 119 ± 18 | 810 ± 125 | 4.5 s |
|  | baked 15 min @ 250° C. | 160 ± 41 | 1198 ± 372 | 5.5 s |
|  | baked 30 min @ 250° C. | 179 ± 17 | 1286 ± 149 | 5 s |
|  | baked 30 min @ 270° C. | 175 ± 40 | 1292 ± 379 | 6 s |
| Shark Skin | N/A* | 227 ± 45 | 1845 ± 400 | 6 s |
| METHAMPHETAMINE (5 ng) | | | | |
| 320A | baked 15 min @ 250° C. | 366 ± 50 | 1491 ± 264 | 2 s |
| 320B | baked 15 min @ 250° C. | 415 ± 25 | 1997 ± 209 | 3 s |
| 326A | baked 15 min @ 250° C. | 431 ± 34 | 1356 ± 99 | 2 s |
| Shark Skin | N/A* | 512 ± 10 | 2897 ± 99 | 3 s |
| HEROIN (50 ng) | | | | |
| 320A | baked 15 min @ 250° C. | 109 ± 15 | 982 ± 220 | 9.5 s |
| 320B | baked 15 min @ 250° C. | 143 ± 10 | 1371 ± 96 | 8 s |
| 326A | baked 15 min @ 250° C. | 75 ± 6 | 558 ± 111 | 10 s |
| Shark Skin | N/A* | 208 ± 9 | 2009 ± 54 | 8 s |

*Baking conditions depend on batch and operating mode
Shark Skin swab data provided for comparison. The last column presents the desorption time at which this intensity is at maximum.

In the positive mode, the 320B Nomex® swab shows the highest sensitivity. Also, among all analytes tested, heroin shows the lowest decrease in sensitivity loss on Nomex® swabs as compared to Shark Skin swabs. This decrease may represent a simple surface effect.

The intensities of the heroin peak resulting from desorption of particles is compared using Nomex® swabs baked at various conditions. The data is provided in Table 8.

TABLE 8

Sensitivity of heroin from solid particles on Nomex ® 326A swabs baked at various conditions.

| Material & baking conditions | Heroin, Max A | Heroin Cum A |
|---|---|---|
| Heroin particles (25 ng) | | |
| Shark Skin | 96 ± 8 | 695 ± 140 |
| Nomex ® 326A, baked 15 min @ 250° C. | 96 ± 11 | 886 ± 36 |
| Nomex ® 326A, baked 30 min @ 250° C. | 92 ± 31 | 928 ± 110 |
| Nomex ® 326A, baked 60 min @ 250° C. | 90 ± 18 | 791 ± 128 |

3. IMS Background in Continuous Wave Mode

Swabs of Nomex® 320B and 326A are selected tested in CW negative and positive modes. The swabs are baked for 15 min at 250° C. No false alarms or ion peaks greater than 50 du are observed.

4. Comparison of Fingerprint Collection Efficiency of Various Nomex® Swabs

The ability to efficiently collect and transfer finger print samples using Nomex® swab material is examined.

This test is performed with C-4 plastic explosive according to the following procedure.

1. Fingerprint Deposition

A finger is rolled three times over C-4 explosive with the force of 1 kg. The finger is then wiped with a Kimwipe® tissue three times, followed by a gentle wash with soap and water. Subsequently, three to five fingerprints are deposited on a suitcase. The suitcase is then swabbed with a cotton swab and analyzed with Ionscan® 400A in order to optimize the amount of C-4 deposited as fingerprint. In case of signal saturation, the finger is washed with soap and water again and the procedure is repeated until a reasonable amount of RDX (about a 500 du signal) is detected by the Ionscan® detector. Subsequently, about 50 fingerprints are deposited on the numbered spots of the suitcase.

2. Fingerprint Collection and Analysis

Fingerprints are swabbed with baked Nomex® material alternating with Shark Skin swabs, e.g., fingerprint #1-Shark Skin, #2-Nomex®, #3-Shark Skin, etc. This procedure allows determination of collection efficiency and comparison between the Nomex® materials and the standard Shark Skin swab. A sampling spoon is also used to collect fingerprint samples. Each swab, after collection, is analyzed immediately using a Sabre Ionscan®. Nomex® 320A, 320B and 326A materials are tested.

5. Comparison of Fingerprint Collection Efficiency Using Hand Vs. Sampling Spoon Fingerprints deposited on suitcase surface according to the procedure described in the previous section are swabbed with Shark Skin swabs by hand alternatively with a sampling spoon. A large scatter of experimental points is observed, particularly with hand sampling, therefore quantification of these data is difficult. When the amount of deposited is high better collection efficiency is observed when the sampling spoon is used to collect the sample. However, when the amount of C-4 in the fingerprint is low, hand collection appears to collect samples more effectively than collection accomplished with a sampling spoon.

It should be noted that during hand collection the spot on the swab contacting the fingerprint surface is exactly matched to the swab area exposed to the Sabre desorber. These controlled conditions are not necessarily present during field operation.

6. Sample Retention Properties of Nomex®

To compare the retention of the collected fingerprint C-4 material on Nomex® materials and Shark Skin swabs, each swab is subjected to several strokes on blank, neutral material after fingerprint sampling (above). During the first series of tests, the fingerprints deposited on suitcase surfaces according to the procedure described above are swabbed alternatively with Shark Skin swabs and Nomex® swabs. After each fingerprint sampling, the swab is rubbed 5 times against blank, neutral suitcase surface and analyzed immediately. On average, Shark Skin swabs show about 20% higher signal than Nomex® swabs.

a. Particle Collection Efficiency Test of Nomex® Material Vs. Shark Skin Swabs

The collection (pick-up) efficiency of explosive particles by Nomex® materials and Shark Skin swabs is tested Two styles of Nomex® material are selected for the test: 320B (thin) and 326A (thick). The Nomex® 320A material is eliminated from further tests as having a more intense background peak ($K_0$=1.4955) in the positive mode (see Table 5) as compared with Nomex® 320B.

Solid particulate is spiked with 5 ng/mg TNT. The particulate is prepared by adding to a 50:50 mixture of $CaCO_3$/silica the appropriate amount of a liquid TNT solution followed by drying and agitation. 5 mg of that spiked particulate is deposited on a rough suitcase surface using a Pasteur pipette to yield a 25 ng TNT deposit. The powder is spread gently using a dental spatula and swabbed with the test swab material using a sampling spoon. The swabs are immediately analyzed by IMS. A calibration curve is prepared using data obtained by direct deposition of different known amounts of TNT powder on the swabs followed by IMS analysis. Table 10 provides a calibration curve for the amount of TNT deposited.

TABLE 10

Calibration curve of TNT powder deposited on Nomex ® 320B swab.

| TNT amount in powder | Max A (du) | Cum A (du) |
|---|---|---|
| 2.5 ng | 135 ± 31 | 1745 ± 472 |
| 5 ng | 239 ± 62 | 3240 ± 829 |
| 12.5 ng | 357 ± 77 | 5188 ± 834 |
| 25 ng | 578 ± 40 | 9143 ± 430 |

The Nomex® 320B and 326A materials show very similar collection efficiencies. Table 11 presents the IMS amplitudes of TNT particles collected by Shark Skin and Nomex® swabs and their sample collection efficiencies calculated on the basis of calibration curve. Sample collection efficiency of TNT particles is approximately 28% for Nomex® and 7% for Shark Skin. These values are calculated using the maximum amplitudes calibration curve.

TABLE 11

IMS amplitudes and pick-up efficiencies of TNT powder particles.

| Material | Max A (du) | Cum A (du) | Pick-up Efficiency Max A | Pick-up Efficiency Cum A |
|---|---|---|---|---|
| Shark Skin | 98 ± 21 | 1096 ± 200 | 7% | 6% |
| Nomex ® 320B | 274 ± 84 | 2792 ± 832 | 29% | 17% |
| Nomex ® 326A | 267 ± 97 | 2402 ± 874 | 27% | 14% |

25 ng TNT powder deposited on swab.

Example 2

Durability and Performance of Nomex® Materials

This example demonstrates the durability and performance of the Nomex® material after extensive usage.
1. Sample Collection Efficiency 200 ng of PETN or 25 ng TNT in the 50:50 CaCO$_3$/silica powder mixture is deposited on a rough suitcase surface and spread gently using a dental spatula. The powder is swabbed with the test material using a sampling spoon and analyzed immediately. After the analysis, the same swab is used to sample a blank suitcase surface ten successive times. Each suitcase sampling consists of the following steps:
1. rubbing the bottom—5 times
2. rubbing the side bottom—5 times
3. rubbing the top—5 times
4. sampling zipper handle
5. sampling each suitcase handle—3 times
6. blank IMS analysis of the swab Blank IMS analyses were performed on a second Sabre system in order to avoid contamination of the test unit.

Next, ten blank suitcase samplings the same swab is used to collect another PETN or TNT powder sample and analyzed immediately (usage #11). The swab is then used to collect ten blank suitcase samples \, as described above. Finally, a third collection and analysis of PETN or TNT powder is performed using the same swab (usage #22).

The variability of signals ranges from 30-35%. No trend in pick-up efficiency is observed between the first to twentieth usage.
2. Comparison of Particle Sensitivity on New and Used Nomex® Swabs During this test, 25 ng of TNT powder is deposited on new Nomex® and on the same material after 22 usages. The data is provided in Table 14. No difference in particle detection sensitivity is observed between new and used Nomex® material. A 1-2 sec shift in time at which the intensity is at a maximum is observed on used swabs.

TABLE 14

Sensitivity of TNT detection on new and used Nomex ® swabs.

| swab | Max A (du) | Cum A (du) | t (max) |
|---|---|---|---|
| Nomex ® 320B, new | 411 ± 116 | 4968 ± 1400 | 4 sec |
| Nomex ® 320B, used | 470 ± 112 | 5530 ± 1487 | 6 sec |
| Nomex ® 326A, used | 461 ± 139 | 5532 ± 1846 | 5 sec |

Example 3

Performance of Nomex® Swab Material at High Temperature

In this example, Nomex® materials are evaluated for use with desorber temperatures of up to 400° C. in both the explosives mode (negative) and the narcotics mode (positive).

Four styles of Nomex® material are considered: 309A, 320A, 320B and 326A.

TABLE 15

Analyte Response in Standard Explosives Mode

| Analyte | TNT 0.3 ng max A | TNT 0.3 ng cum A | PETN 0.5 ng max A | PETN 0.5 ng cum A | HMTD 5 ng max A | HMTD 5 ng cum A | AN 20 ng max A | AN 20 ng cum A |
|---|---|---|---|---|---|---|---|---|
| Fiberglass/Teflon | 158 ± 21 | 935 ± 105 | 404 ± 31 | 2573 ± 275 | 231 ± 18 | 1376 ± 9 | 1236 ± 128 | 8638 ± 2042 |
| 309A baked | 448 ± 17 | 2296 ± 175 | 474 ± 28 | 2953 ± 337 | 456 ± 27 | 4810 ± 104 | 687 ± 30* | 8453 ± 962* |
| 320A baked | 581 ± 16 | 2716 ± 130 | 511 ± 21 | 3305 ± 182 | 280 ± 74 | 2313 ± 286 | 1149 ± 54 | 17076 ± 3447 |
| 320B baked | 557 ± 32 | 2732 ± 363 | 458 ± 16 | 3145 ± 161 | | | | |
| 326A baked | 616 ± 57 | 3033 ± 436 | 471 ± 14 | 3659 ± 112 | 247 ± 43 | 2619 ± 188 | 855 ± 82 | 12086 ± 2951 |

*10 ng solution was used
Values are the average of three experiments.

TABLE 16

Analyte Response in Narcotics Mode for Teflon and Nomex ® 326A

| Substrate | Cocaine (0.5 ng) | | Heroin (3 ng) | | Methamphetamine (0.6 ng) | |
|---|---|---|---|---|---|---|
| | max A | cum A | max A | cum A | max A | cum A |
| Teflon | 178 ± 12 | 1271 ± 133 | 267 ± 23 | 1756 ± 242 | 217 ± 29 | 1376 ± 190 |
| 326A | 224 ± 4 | 983 ± 175 | 197 ± 5 | 1063 ± 209 | 139 ± 9 | 267 ± 29 |

Nomex® 320B and 326A are selected for further investigation as a swab material high temperature application in Ionscan® instruments. Nomex® 309A is much thinner than either 320B or A and is useful for some applications, including those applications using an automatic sampling method, such as document scanners and the like.

A comparative study between cotton and Nomex® swabs is carried out as described in Example 1. The results of this comparison show that fingerprints are picked-up slightly better with Nomex® material than with a cotton swab, and particle pick-up is about the with the two types of material. Particle retention is about the same for Nomex® 326A, Nomex® 320B and cotton.

Nomex® 320B, Nomex® 326A and cotton swabs are tested for durability tests at high desorber temperatures. Swabs of these materials were used to collect explosives particles in silica mixture from a constant amount of powder deposited on suitcase patches as described in Example 2.

Swabs comprising Nomex® or a blend of Nomex® and Kevlar® function effectively at desorber temperatures of 400° C. When exposed to a 400° C. desorber for a prolonged time (more than 4 s) both the Nomex® and the Nomex®/Kevlar® blend materials show some deterioration after a few desorption cycles. However, when desorption time is maintained at under 4 s, tests involving more than twenty desorption cycles indicates that when exposure to 400° C. desorber is maintained at under 4 s/cycle, the Nomex® and Nomex®/Kevlar® blend materials both are suitable for the high temperature application.

Example 4

Suitability of Nomex Swab for Pharmaceutical Cleaning Verification

This example demonstrates the pickup properties of Nomex swabs in swiping tests of 10 ng of buspirone-HCl deposited on a stainless steel surface of the same type used in pharmaceutical manufacturing vessels.

Samples are analyzed using a Smiths Ionscan LS IMS spectrometer. A standard solution of buspirone-HCl is prepared in isopropanol at a concentration of 4 ng/μl solution. 10 ng is deposited on polished stainless steel sheet, simulating the walls of a mixing vessel. Using a hand-spoon with a Nomex swab, the surface is briefly wiped. The swab is then thermally desorbed into the IMS spectrometer. As a control, 10 ng is deposited directly onto a Nomex swab.

Nomex style 320A (DuPont™) with typical thickness 0.10 mm, basic weight 67.8 g/m² and density of 0.71 g/cc is used as the swab material.

Figure 3:
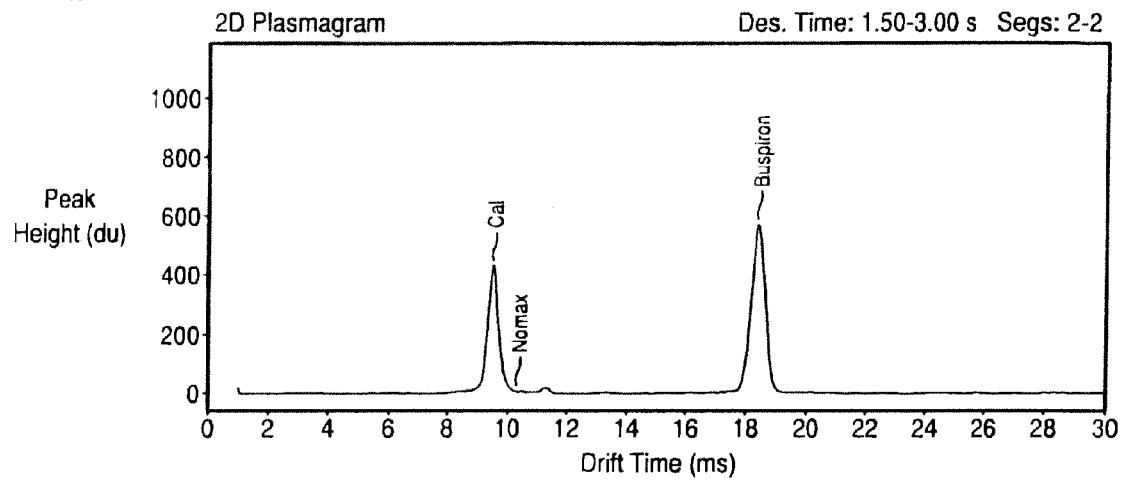
FIG. 3. Plasmagram of 10 ng buspiron in isopropanol deposited onto a Nomex swab. Data is obtained using an Ionscan® LS or Ionscan® 400B ion mobility spectrometer (Smiths Detection).
Figure 3:
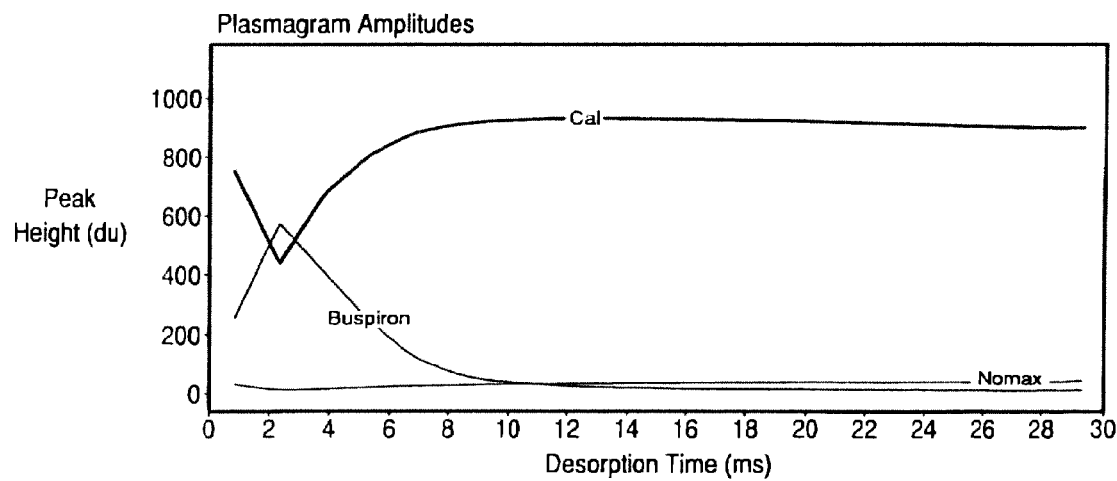
Figure 4:
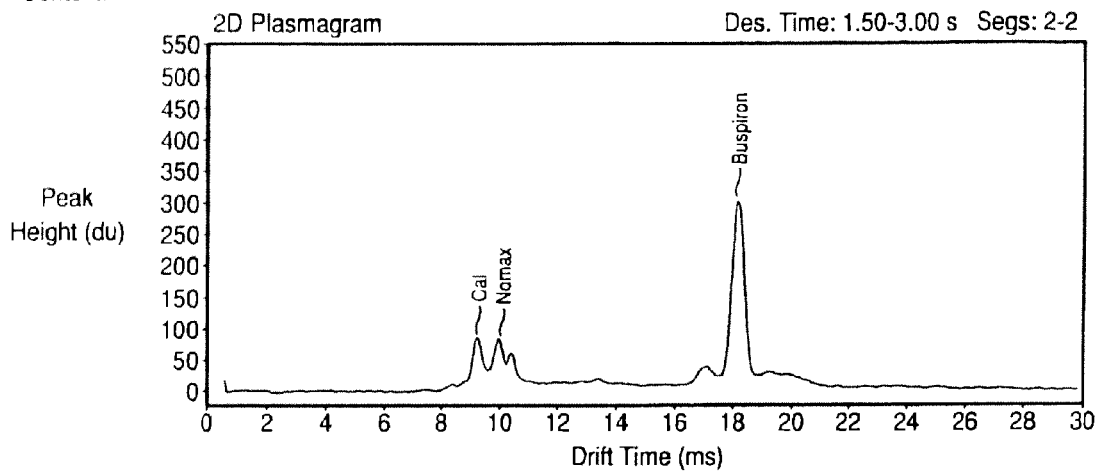
FIG. 4. Plasmagram obtained by swiping with a Nomex swab polished stainless onto which 10 ng in isopropanol is deposited.

FIG. 3 shows a typical calibration run of 10 ng of buspirone desorbed from a Nomex swab. FIG. 4 is a plasmagram obtained by swiping a piece of polished stainless onto which 10 ng is deposited as described above. In both experiments, a Nomex-related contaminant peak, labeled "Nomex" in the plasmagram, is observed. The peak decreases in amplitude as the material repeatedly heated. A buspirone protonated peak appears at $K_0=0.9627$ or drift time 18.393 ms. A summary of the data is shown in Table 17.

TABLE 17

Summary of calibration and Wipe tests

Maximum Amplitude (du)

| | Sample 1 | Sample 2 | Sample 3 | Average |
|---|---|---|---|---|
| 10 ng Buspiron Direct deposit | 254 | 279 | 285 | 272 (6%) du |

| | Sample 1 | Sample 2 | Sample 3 | Sample 4 | Average |
|---|---|---|---|---|---|
| 10 ng Buspiron Wiped from steel surface | 219 | 122 | 125 | 171 | 159 (29%) du |

Average Transfer Efficiency = 58%

Nomex fabric displays superior properties as compared to cotton fabric in swab applications. Nomex fabric tolerates much higher temperatures and shows less contaminant than cotton fabric. Preliminary testing shows good pickup for a pharmaceutical drug at average efficiency of 58%. Reproducibility of the method for harvesting the sample from stainless steel surface is high at 29% for an average of four runs.

While the invention is described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention. All references and publications cited herein are incorporated by reference in their entireties.

What is claimed is:

1. A method
providing a sampling swab that comprises an aromatic polyamide fabric having a porous surface configured to capture trace particulate matter from a surface of an object; and
before the sampling swab is used for sampling purposes, baking the aromatic polyamide fabric at a temperature of at least approximately 200° C. for a time of at least approximately 6 minutes, thereby reducing an amount of a contaminant resulting from manufacture of the aromatic polyamide fabric.

2. The method of claim 1, further comprising spinlacing fibers to form the fabric.

3. The method of claim 1, wherein the contaminant is a nitrate associated with manufacture of aromatic polyamide fibers.

4. The method of claim 1, further comprising, before the sampling swab is used for sampling purposes, testing the swab.

5. The method of claim 1, wherein the aromatic polyamide fabric is baked at temperature that is lower than a temperature at which fibers that form the aromatic polyamide fabric thermally decompose and higher than a temperature used to thermally desorb vapor from the particulate matter collected by the swab during use.

6. The method of claim 1, wherein the contaminant at least partially masks detection of at least one of an explosive and a narcotic.

7. The method of claim 1, wherein the contaminant is not an explosive or a narcotic, but is associated with a peak in an ion mobility spectrometry plasmagram that is also associated with an explosive or a narcotic.

8. The method of claim 1, further comprising thermally desorbing at least some material from the swab using a thermal desorber included in an ion mobility spectrometer to test for presence of the contaminant.

9. The method of claim 1, wherein the aromatic polyamide fabric comprises at least one of Nomex® 309B, Nomex® 309A, Nomex® 320B, Nomex® 320A, and Nomex® 326A.

10. The method of claim 1, wherein the aromatic polyamide fabric comprises Nomex® 320B.

11. The method of claim 1, wherein the aromatic polyamide fabric is baked at a temperature of at least approximately 400° C. for a time of at least approximately 6 minutes.

12. The method of claim 1, wherein the aromatic polyamide fabric is baked at a temperature of approximately 200° C. for a time of at least approximately 10 minutes.

13. The method of claim 1, wherein the aromatic polyamide fabric is baked at a temperature of approximately 200° C. for a time of approximately 10 minutes.

14. The method of claim 1, wherein the aromatic polyamide fabric is baked at a temperature of approximately 250° C. for a time of at least approximately 15 minutes.

15. The method of claim 1, wherein the aromatic polyamide fabric is baked at a temperature of approximately 250° C. for a time of approximately 15 minutes.

16. The method of claim 1, wherein the sampling swab has a weight per unit area of between approximately 0.010 g/cm$^2$ and approximately 0.8 g/cm$^2$.

17. The method of claim 16, wherein the sampling swab has a thickness of between approximately 0.01 cm and approximately 0.03 cm.

\* \* \* \* \*